US012577518B2

(12) United States Patent
Rhodes et al.

(10) Patent No.: US 12,577,518 B2
(45) Date of Patent: Mar. 17, 2026

(54) BIOLOGICAL INDICATOR FOR USE WITH A LIQUID STERILANT

(71) Applicant: ASP Global Manufacturing GMBH, Schaffhausen (CH)

(72) Inventors: Sam J. Rhodes, Los Angeles, CA (US); Navid Omidbakhsh, Mission Viejo, CA (US); Doug V. Truong, Irvine, CA (US)

(73) Assignee: ASP Global Manufacturing GmbH (CH)

( * ) Notice: Subject to any disclaimer, the term of this patent is extended or adjusted under 35 U.S.C. 154(b) by 1036 days.

(21) Appl. No.: 17/761,392

(22) PCT Filed: Sep. 19, 2020

(86) PCT No.: PCT/IB2020/058750
§ 371 (c)(1),
(2) Date: Mar. 17, 2022

(87) PCT Pub. No.: WO2021/053627
PCT Pub. Date: Mar. 25, 2021

(65) Prior Publication Data
US 2022/0372424 A1     Nov. 24, 2022

Related U.S. Application Data

(60) Provisional application No. 62/903,540, filed on Sep. 20, 2019.

(51) Int. Cl.
*C12M 1/12* (2006.01)
*A61L 2/28* (2006.01)
*C12Q 1/22* (2006.01)

(52) U.S. Cl.
CPC ............... *C12M 37/06* (2013.01); *A61L 2/28* (2013.01); *C12Q 1/22* (2013.01); *A61L 2202/24* (2013.01)

(58) Field of Classification Search
None
See application file for complete search history.

(56) References Cited

U.S. PATENT DOCUMENTS

| | | | |
|---|---|---|---|
| 2,447,988 A | 8/1948 | Pierson |
| 3,346,464 A | 10/1967 | Ernst |

(Continued)

FOREIGN PATENT DOCUMENTS

| | | | |
|---|---|---|---|
| CA | 738687 A | 7/1966 |
| CA | 823163 A | 9/1969 |

(Continued)

OTHER PUBLICATIONS

Namsa, Self-Contained Biological Indicators for Monitoring Steam, Northwood, Ohio, 2015.

(Continued)

*Primary Examiner* — Holly Kipouros
(74) *Attorney, Agent, or Firm* — Lerner David LLP

(57) ABSTRACT

A biological indicator (100) for use in a liquid-chemical decontamination system is disclosed. The biological indicator may include a housing (102) and a cap (106) coupled to the housing. The cap may comprise a liquid chamber and at least two ports. One of the ports may connect to a liquid passage in the cap such that liquids such as liquid-chemical decontaminants may be introduced and removed from the biological indicator via this port.

23 Claims, 5 Drawing Sheets

(56) References Cited

U.S. PATENT DOCUMENTS

| | | | |
|---|---|---|---|
| 3,450,319 A | 6/1969 | Ray et al. | |
| 3,752,743 A | 8/1973 | Henshilwood | |
| 3,948,727 A | 4/1976 | Steiger | |
| 4,291,122 A | 9/1981 | Orelski | |
| 4,304,869 A | 12/1981 | Dyke | |
| 4,528,268 A | 7/1985 | Andersen et al. | |
| 4,537,099 A | 8/1985 | Oster et al. | |
| 4,546,086 A | 10/1985 | Hounsell | |
| 4,579,823 A | 4/1986 | Ryder | |
| 4,637,139 A | 1/1987 | Chen | |
| 4,717,661 A | 1/1988 | McCormick et al. | |
| 4,732,850 A | 3/1988 | Brown et al. | |
| 4,741,437 A | 5/1988 | Gorski et al. | |
| 4,839,291 A | 6/1989 | Welsh et al. | |
| 4,883,641 A | 11/1989 | Wicks et al. | |
| 4,885,253 A | 12/1989 | Kralovic | |
| 5,028,543 A | 7/1991 | Finch et al. | |
| 5,073,488 A | 12/1991 | Matner et al. | |
| 5,167,923 A | 12/1992 | Van Iperen | |
| 5,223,401 A | 6/1993 | Foltz et al. | |
| 5,252,484 A | 10/1993 | Matner et al. | |
| 5,293,816 A | 3/1994 | Musumeci, Sr. et al. | |
| 5,362,654 A | 11/1994 | Pouletty | |
| 5,405,580 A | 4/1995 | Palmer | |
| 5,415,994 A | 5/1995 | Imrich et al. | |
| 5,418,167 A | 5/1995 | Matner et al. | |
| 5,482,171 A | 1/1996 | Palmer | |
| 5,516,648 A | 5/1996 | Malchesky et al. | |
| 5,552,320 A | 9/1996 | Smith | |
| 5,736,355 A | 4/1998 | Dyke et al. | |
| 5,739,004 A | 4/1998 | Woodson | |
| 5,750,184 A | 5/1998 | Mburgia | |
| 5,759,848 A | 6/1998 | Nagoshi et al. | |
| 5,770,393 A | 6/1998 | Dalmasso et al. | |
| 5,801,010 A | 9/1998 | Falkowski et al. | |
| 5,830,683 A | 11/1998 | Hendricks et al. | |
| 5,863,790 A | 1/1999 | Bolea | |
| 5,866,356 A | 2/1999 | Albert et al. | |
| 5,942,438 A | 8/1999 | Antonoplos et al. | |
| 6,218,189 B1 | 4/2001 | Antonoplos et al. | |
| 6,436,659 B1 | 8/2002 | Hui et al. | |
| 6,458,554 B1 | 10/2002 | Hui et al. | |
| 6,551,555 B2 | 4/2003 | Antonoplos et al. | |
| 6,924,139 B2 | 8/2005 | Eveland et al. | |
| 7,091,042 B2 | 8/2006 | Lemus et al. | |
| 7,247,482 B2 | 7/2007 | Lemus et al. | |
| 7,642,067 B2 | 1/2010 | Song et al. | |
| 8,173,388 B2 | 5/2012 | Pasmore et al. | |
| 8,173,418 B2 | 5/2012 | Sestak et al. | |
| 8,173,438 B1 | 5/2012 | Putnam et al. | |
| 8,765,398 B2 | 7/2014 | Dalmasso | |
| 8,840,837 B2 | 9/2014 | Smith et al. | |
| 8,915,413 B2 | 12/2014 | Kayser | |
| 8,945,837 B2 | 2/2015 | Franciskovich et al. | |
| 8,969,029 B2 | 3/2015 | Chandrapati et al. | |
| 8,980,622 B2 | 3/2015 | Smith et al. | |
| 9,145,573 B2 | 9/2015 | Pederson et al. | |
| 9,321,973 B2 | 4/2016 | Marchand et al. | |
| 9,322,046 B2 | 4/2016 | Chandrapati et al. | |
| 9,525,317 B2 | 12/2016 | Ohashi et al. | |
| 9,675,722 B2 | 6/2017 | Ahimou et al. | |
| 9,856,124 B2 | 1/2018 | Mitidieri | |
| 10,059,977 B2 | 8/2018 | Witcher et al. | |
| 10,150,901 B2 | 12/2018 | Boutier et al. | |
| 10,561,753 B2 | 2/2020 | Thompson et al. | |
| 2003/0153895 A1* | 8/2003 | Leinsing | A61J 1/2089 |
| | | | 604/403 |
| 2004/0197848 A1 | 10/2004 | Behun et al. | |
| 2005/0014214 A1 | 1/2005 | Eveland et al. | |
| 2008/0070272 A1 | 3/2008 | Franciskovich et al. | |
| 2009/0068716 A1 | 3/2009 | Hirota et al. | |
| 2009/0317312 A1* | 12/2009 | Mikuski | C02F 1/685 |
| | | | 422/265 |
| 2010/0081165 A1 | 4/2010 | Pasmore et al. | |
| 2011/0182770 A1* | 7/2011 | Chandrapati | C12Q 1/22 |
| | | | 422/292 |
| 2011/0200992 A1 | 8/2011 | Chandrapati et al. | |
| 2012/0149094 A1 | 6/2012 | Smith et al. | |
| 2012/0156090 A1 | 6/2012 | Dane et al. | |
| 2013/0210048 A1 | 8/2013 | Chandrapati et al. | |
| 2013/0210069 A1 | 8/2013 | Pederson et al. | |
| 2013/0217107 A1 | 8/2013 | Pederson et al. | |
| 2013/0224849 A1 | 8/2013 | Chandrapati et al. | |
| 2013/0273594 A1 | 10/2013 | Ahimou et al. | |
| 2013/0302849 A1* | 11/2013 | Smith | C12Q 1/22 |
| | | | 435/31 |
| 2014/0273072 A1 | 9/2014 | Franciskovich et al. | |
| 2015/0004682 A1 | 1/2015 | Smith et al. | |
| 2015/0167047 A1 | 6/2015 | Smith et al. | |
| 2015/0337354 A1 | 11/2015 | Ahimou et al. | |
| 2016/0000954 A1 | 1/2016 | Ahimou et al. | |
| 2017/0175071 A1 | 6/2017 | Sullivan et al. | |
| 2017/0211035 A1 | 7/2017 | Yirava et al. | |
| 2017/0253845 A1 | 9/2017 | Amin | |
| 2018/0015193 A1 | 1/2018 | Swaminathan et al. | |
| 2018/0071421 A1 | 3/2018 | Fang et al. | |
| 2018/0187142 A1 | 7/2018 | Troung | |
| 2018/0237821 A1 | 8/2018 | Fryer | |
| 2018/0245122 A1 | 8/2018 | Soto et al. | |
| 2019/0002951 A1 | 1/2019 | Fryer et al. | |
| 2019/0106725 A1 | 4/2019 | Cregger et al. | |
| 2019/0106726 A1 | 4/2019 | Cregger et al. | |
| 2019/0169672 A1 | 6/2019 | Fryer et al. | |
| 2020/0123492 A1* | 4/2020 | Lombardia | C12M 23/06 |
| 2020/0165658 A1 | 5/2020 | Bala et al. | |
| 2021/0147784 A1 | 5/2021 | Amin | |

FOREIGN PATENT DOCUMENTS

| | | |
|---|---|---|
| CA | 1 182 729 A | 2/1985 |
| CN | 1853734 A | 11/2006 |
| CN | 201453688 U | 5/2010 |
| CN | 102170915 A | 8/2011 |
| CN | 102596261 A | 7/2012 |
| CN | 203307339 U | 11/2013 |
| CN | 105087361 A | 11/2015 |
| CN | 204814967 U | 12/2015 |
| CN | 105561362 A | 5/2016 |
| CN | 106267277 A | 1/2017 |
| CN | 106966348 A | 7/2017 |
| CN | 206473580 U | 9/2017 |
| CN | 206970617 U | 2/2018 |
| EP | 0 152 298 A2 | 8/1985 |
| EP | 1032822 B1 | 5/2003 |
| EP | 2968634 B1 | 12/2016 |
| FR | 2708287 B1 | 10/1995 |
| GB | 1055387 A | 1/1967 |
| IN | 201747012748 A | 4/2017 |
| IN | 201714046902 A | 7/2018 |
| JP | H10201466 A | 8/1998 |
| JP | H11196893 A | 7/1999 |
| JP | 2006-521818 A | 9/2006 |
| JP | 2012-503994 A | 2/2012 |
| JP | 2013-542786 A | 11/2013 |
| JP | 2014-501553 A | 1/2014 |
| JP | 2016-516404 A | 6/2016 |
| JP | 2017123976 A | 7/2017 |
| JP | 2018201397 A | 12/2018 |
| RU | 129814 U1 | 7/2013 |
| RU | 143648 U1 | 7/2014 |
| RU | 146719 U1 | 10/2014 |
| RU | 2683644 C2 | 4/2019 |
| WO | 92/19764 A1 | 11/1992 |
| WO | 97/35189 A1 | 9/1997 |
| WO | 00/50634 A1 | 8/2000 |
| WO | 2005/036128 A2 | 4/2005 |
| WO | 2008/106327 A2 | 9/2008 |
| WO | 2010/039388 A2 | 4/2010 |
| WO | 2010/045138 A2 | 4/2010 |
| WO | 2016/057520 A1 | 4/2016 |
| WO | 2016/205953 A1 | 12/2016 |
| WO | 2018/025207 A1 | 2/2018 |

(56)                    References Cited

FOREIGN PATENT DOCUMENTS

| WO | 2018/160449 | A1 | 9/2018 |
| WO | 2020/136463 | A1 | 7/2020 |
| WO | 2021/053627 | A1 | 3/2021 |

OTHER PUBLICATIONS

Anonymous, 3M™ Attest™ 1292E Rapid Readout Biological Indicator, Internet Article, Jan. 1, 1999, http://multimedia.3m.com/mws/mediawebserver?mwsId=SSSSSu7zK1fslxtU48_el8mGev7qe17zHvTSevTSeSSSSSS--&fn=Rapid_Readout_Profile_1292E.pdf.

Chinese First Office Action and Search Report for Chinese Patent Application No. 201810004516.1 issued on Aug. 3, 2020 and English translation.

PCT Notification of Transmittal of the International Search Report and the Written Opinion of the International Searching Authority, or the Declaration for International Application No. PCT/IB2020/058750 date of mailing Nov. 27, 2020, 1 page.

PCT Written Opinion of the International Searching Authority for International Application No. PCT/IB2020/058750 date of mailing Nov. 27, 2020, 6 pages.

PCT International Search Report for International Application No. PCT/IB2020/058750 date of mailing Nov. 27, 2020, 6 pages.

Russian Search Report for Registration No. 2017145872/04(078515) date of application Dec. 26, 2017, date of valid search completion: Jun. 10, 2021, 2 pages.

PCT Notification of Transmittal of the International Search Report and the Written Opinion of the International Searching Authority, or the Declaration for International Application No. PCT/IB2021/060235, date of mailing Feb. 18, 2022, 9 pages.

Chinese Search Report issued in Appln. No. 202080065486.0 dated May 31, 2023 (3 pages).

* cited by examiner

BIOLOGICAL INDICATOR FOR USE WITH A LIQUID STERILANT

CROSS-REFERENCE TO RELATED APPLICATIONS

The present application is a U.S. National Phase Application of International Application No. PCT/IB2020/058750, filed Sep. 19, 2020, which claims priority to U.S. Provisional Patent Application No. 62/903,540, filed Sep. 20, 2019. The entire contents of these applications are incorporated by reference herein in their entirety.

FIELD

The subject matter disclosed herein relates to biological indicators, particularly those suitable for use in liquid-chemical decontamination systems and procedures for disinfection or sterilization.

BACKGROUND

Certain instruments, e.g., medical instruments, should be reprocessed, i.e., decontaminated, between medical procedures in which they are used to avoid causing infection or illness in a subject. Two decontamination methods pertinent to the present disclosed subject matter include disinfection and liquid-chemical sterilization. Both types of procedures may include steps of removing foreign material from the endoscope, cleaning the endoscope, introducing a disinfectant solution or a liquid-chemical sterilant to the endoscope, rinsing the endoscope, and drying the endoscope A decontamination indicator is a device that may be placed alongside or in proximity to a medical device being subject to a decontamination procedure, such that the decontamination indicator is subject to the same decontamination cycle as the medical device. For instance, a biological indictor having a predetermined quantity of microorganisms possessing known resistance to the sterilant may be placed into a sterilization chamber alongside a medical device and subjected to a sterilization cycle. After the sterilization procedure is complete, the microorganisms in the biological indicator may be cultured to determine whether any of the microorganisms survive.

Biological indicators often include a housing that contains a quantity of microorganisms and a source of growth media in a frangible container that is located near the microorganisms. Following a sterilization procedure, the frangible container may be broken to release the growth media and culture any surviving microorganisms in situ. The indicator may then be incubated at elevated temperatures, typically around 50° C. to 60° C., which encourages outgrowth of the surviving microorganisms.

The frangible container, e.g., ampule, that contains the liquid growth medium is often fabricated from glass. The glass must be sufficiently robust to avoid breakage during transportation, e.g., from the manufacturer of the biological indicator to a health care provider. Such robustness, however, corresponds to a greater force required to break the ampule at the desired time by medical personnel. Accordingly, some manufacturers provide activation devices to hospital personnel to assist them in breaking the ampule.

SUMMARY OF THE DISCLOSURE

A biological indicator for use in a liquid-chemical decontamination system is disclosed. The biological indicator may include a housing defining a longitudinal axis and having a first port. A cap may be coupled to the housing. A first portion of the cap may be disposed outside the housing, while a second portion of the cap may be disposed at least partially inside the housing. The second portion of the cap may include a liquid chamber comprising a second port and containing a growth medium. The second port may be disposed in the housing about the longitudinal axis of the housing. A seal may cover the second port to define a bottom boundary of the liquid chamber. Further, the second portion of the cap may comprise a sidewall including a round portion and a flat portion, the sidewall of the second portion defining a side boundary of the liquid chamber.

The cap may also include a third port and a liquid passage that extends through a space disposed between the sidewall of the second portion of the cap, e.g., the flat portion thereof, and an inside surface of the housing. As such, liquids such as liquid-chemical decontaminants may be introduced and removed from the biological indicator via the third port.

The biological indicator may also include an insert disposed in the housing. The insert may have a tip portion, e.g., a spike, disposed along the longitudinal axis, for puncturing the seal. As such, an ampule containing a growth medium is not disposed in the housing.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

Figure 1:
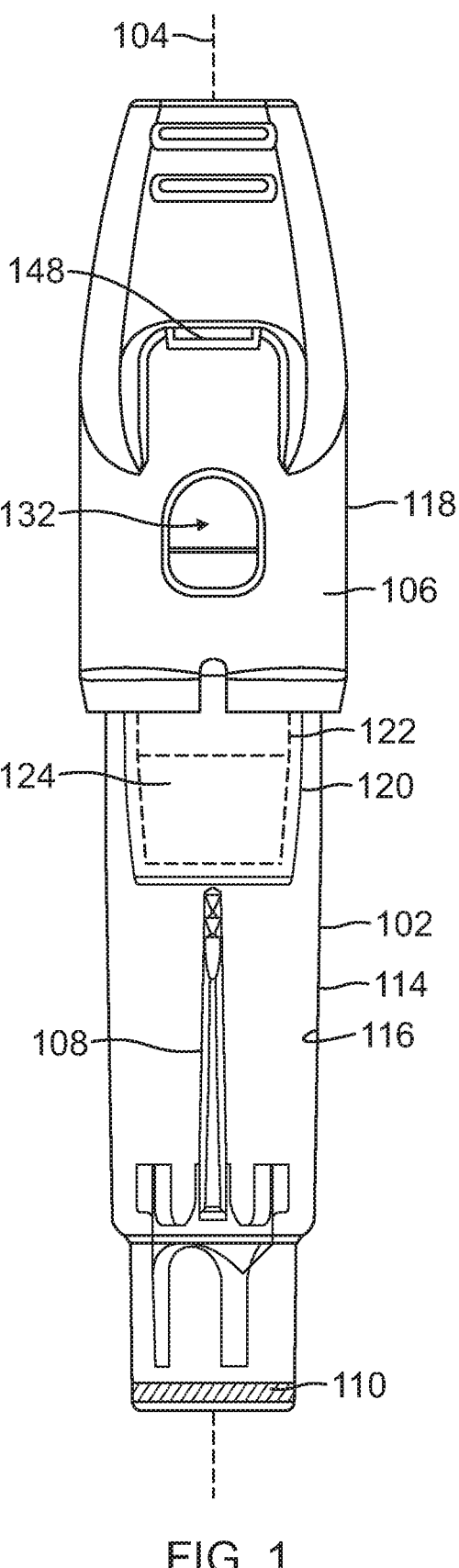
FIG. 1 depicts a front view of a biological indicator.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Commercially available biological indicators are typically used in sterilization procedures that utilize gaseous sterilants, e.g., ethylene oxide and hydrogen peroxide. Such procedures often involve positioning medical devices alongside a sterilization indicator in a vacuum chamber of a sterilization system. After a vacuum (e.g., less than five torr) is drawn in the chamber, the gaseous sterilant may be introduced into the chamber, which raises the pressure in the chamber, such that gaseous sterilant will enter into the biological indicator. Subsequently, the gaseous sterilant is removed from the biological indicator and the chamber by drawing a vacuum, venting the chamber, or both.

A biological indicator suitable for use in decontamination procedures that utilize liquid-chemical decontaminants is disclosed. Such decontamination procedures may include disinfection procedures that utilize a liquid-chemical disinfectant, e.g., a solution comprising ortho-Phthalaldehyde, and sterilization procedures that utilize liquid-chemical sterilants, e.g., a solution comprising peracetic acid. As such, ortho-Phthalaldehyde solutions and peracetic acid solutions may be considered examples of liquid-chemical decontaminants or decontaminant solutions. During a decontamination procedure, but after an instrument and a biological indicator have been exposed to a liquid decontaminant for a suitable amount of time, the liquid decontaminant must be removed from the instrument and the biological indicator. There are various reasons that the liquid decontaminant must be removed from the biological indicator. For example, removal helps avoid injury to healthcare personnel that might be caused by skin contact with the decontaminant. Removal of the decontaminant also enables an accurate assessment of microbial outgrowth in the biological indicator after the decontamination procedure has ended.

FIGS. 1-4 reflect a biological indicator 100 that is suitable for use in a decontamination procedure that utilizes a liquid decontaminant. Biological indicator 100 includes a housing 102 defining a longitudinal axis 104 of biological indicator 100, a cap 106, an insert 108, and a source of microorganisms or active enzymes, such as carrier 110.

Housing 102 may have an elongate cylindrical form and may include a first port 112, an outside surface 114, and an inside surface 116. Cap 106 may be coupled to housing 102 such that cap 106 covers first port 112.

Figure 5:
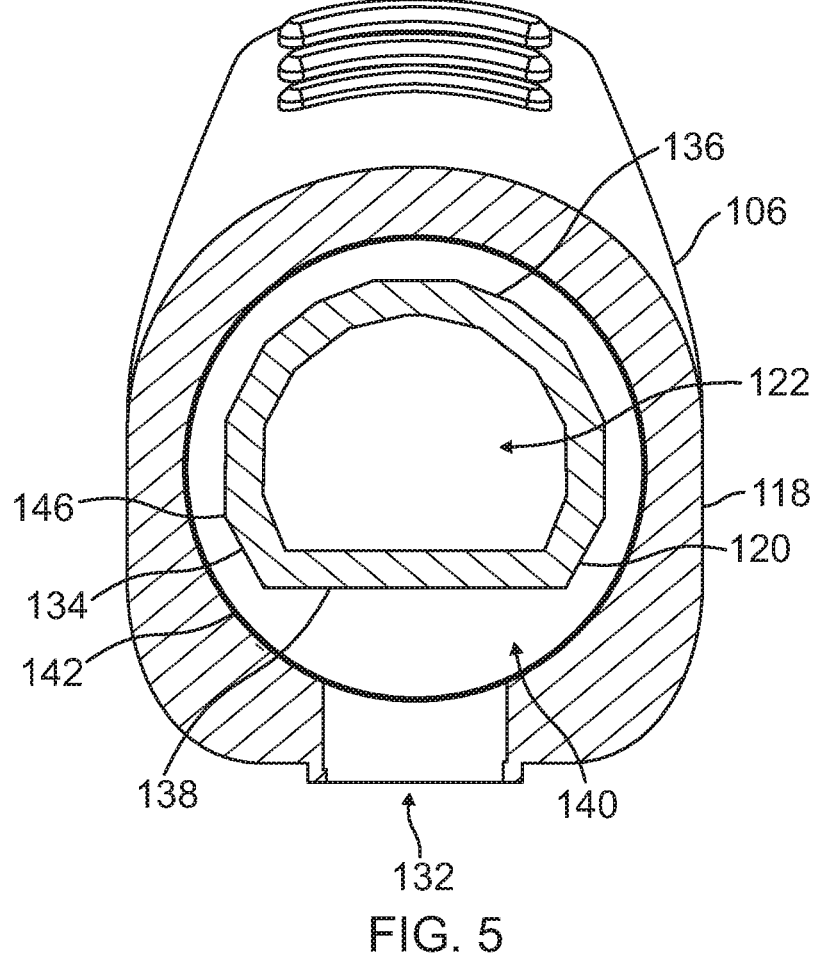
FIG. 5 depicts a cross-sectional view of a cap of the biological indicator taken along line 5-5 in FIG. 4.

With additional reference to FIG. 5, cap 106 may comprise a first portion 118 and a second portion 120 that define an annular recess 140 therebetween. A top portion of housing 102 that includes first port 112 may be disposed in recess 140 such that cap 106 covers first port 112. As such an inner surface 142 of first portion 118 may contact outer surface 114 of housing 102, thus coupling housing 102 and cap 106 by a friction fit. For example, inner surface 142 and outer surface 114 may each have diameters of between about 10 millimeters and 15 millimeters, provided that the diameter of inner surface 142 is slightly less than the diameter of outer surface 114, e.g., about 0.1 millimeters and about 2 millimeters less. For example, inner surface 142 may have a diameter of about 12.5 millimeters and outer surface 114 may have a diameter of about 12.6 millimeters.

Notably, biological indicator 100 lacks an ampule containing a growth medium, which the inventors have found impedes introduction and removal of liquids (e.g., decontaminant, neutralizer) into and from housing 102. As such, the inventors designed biological indicator 100 such that second portion 120 of cap 106 may include a liquid chamber 122 containing a growth medium 124. Liquid chamber 122 may include a second port 126 covered by a seal 128 such that seal 128 defines a bottom boundary 130 of liquid chamber 122. As cap 106 is coupled to housing 102, second portion 120 is disposed at least partially inside housing 102 such that seal 128 and bottom boundary 130 of liquid chamber 122 are disposed inside housing 102. Second portion 120 may also include a sidewall 134 that forms a side boundary 146 of liquid chamber 122. Sidewall 134 may comprise a round portion 136 and a flat portion 138. Accordingly, recess 140 between first portion 118 and second portion 120 is larger proximate to flat portion 138 than proximate to round portion 136. For example, the distance between inside surface 116 of housing 102 and round portion 136 of sidewall 134 may be between approximately 0.1 millimeters and approximately 0.2 millimeters, whereas the distance between inside surface 116 of housing 102 and flat portion 138 of sidewall 134 may be between approximately 1 millimeter and approximately 3 millimeters. For example, the distance between inside surface 116 of housing 102 and round portion 136 of sidewall 134 may be approximately 0.13 millimeters, whereas the distance between inside surface 116 of housing 102 and flat portion 138 of sidewall 134 may be approximately 2 millimeters.

Figure 2:
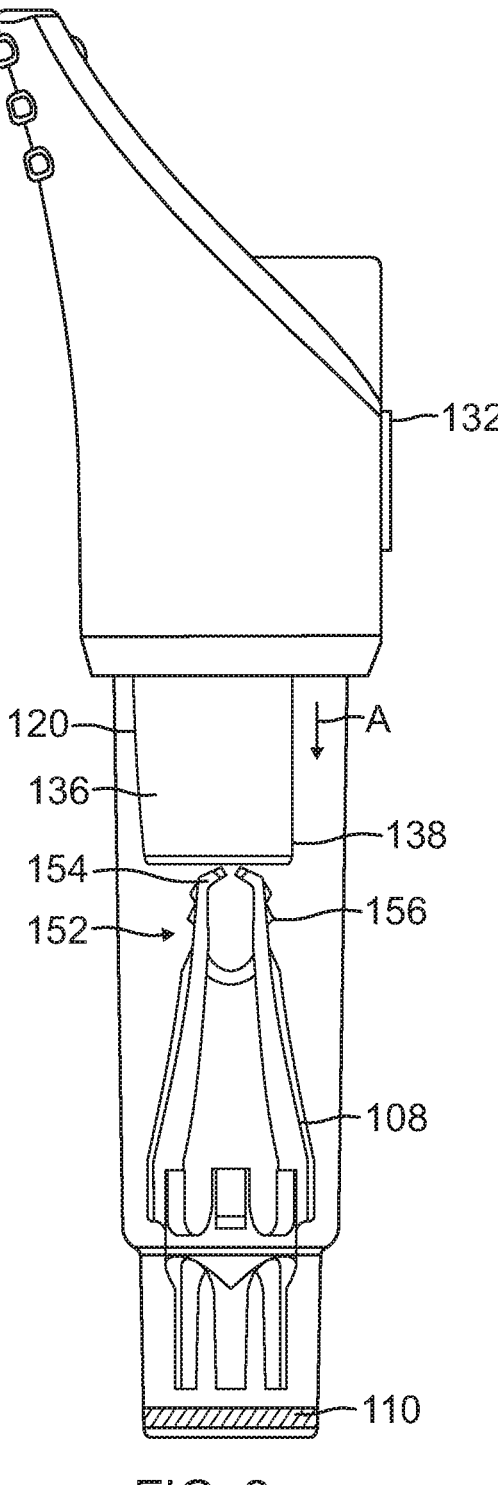
FIG. 2 depicts a side view of the biological indicator.
Figure 3:
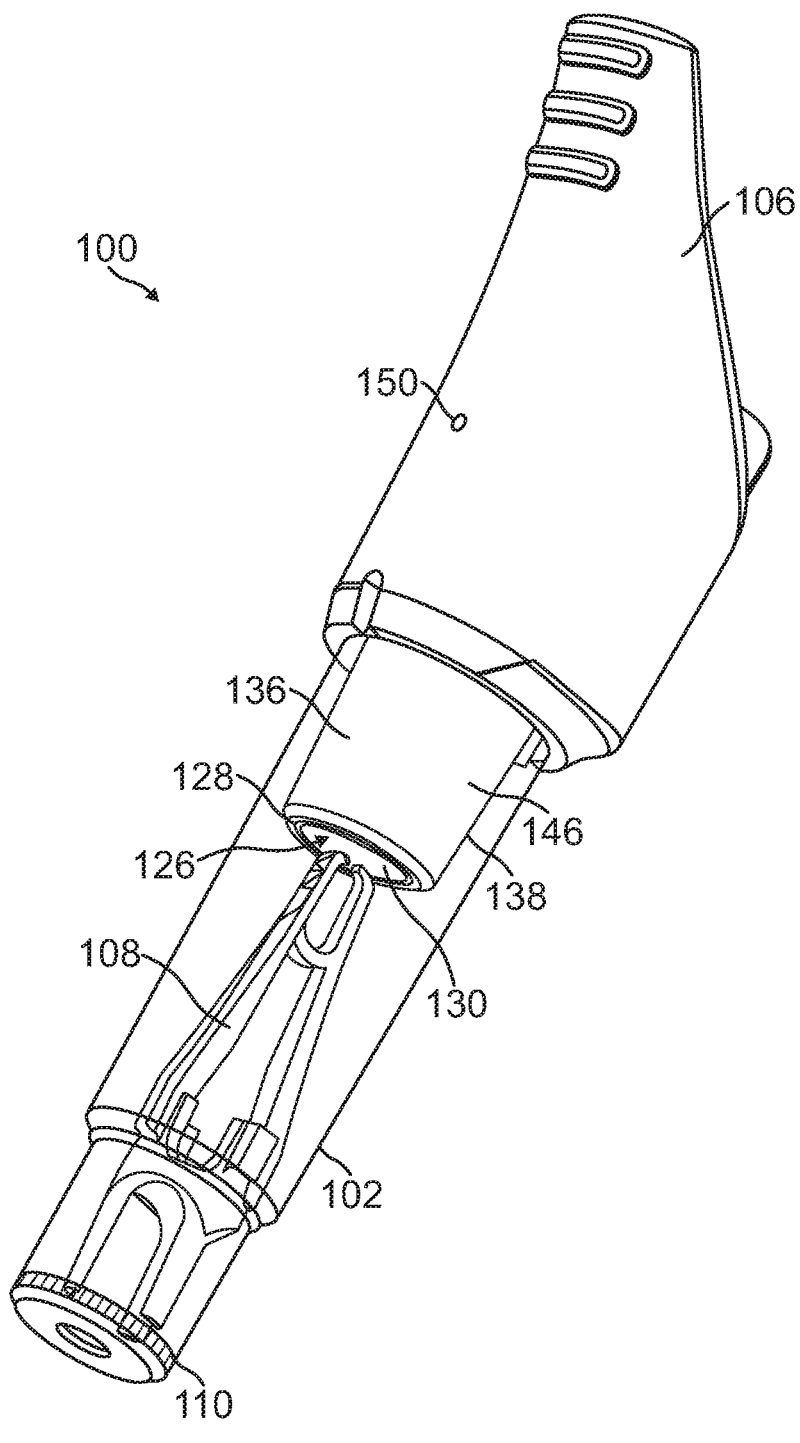
FIG. 3 depicts a perspective view of the biological indicator.
Figure 4:
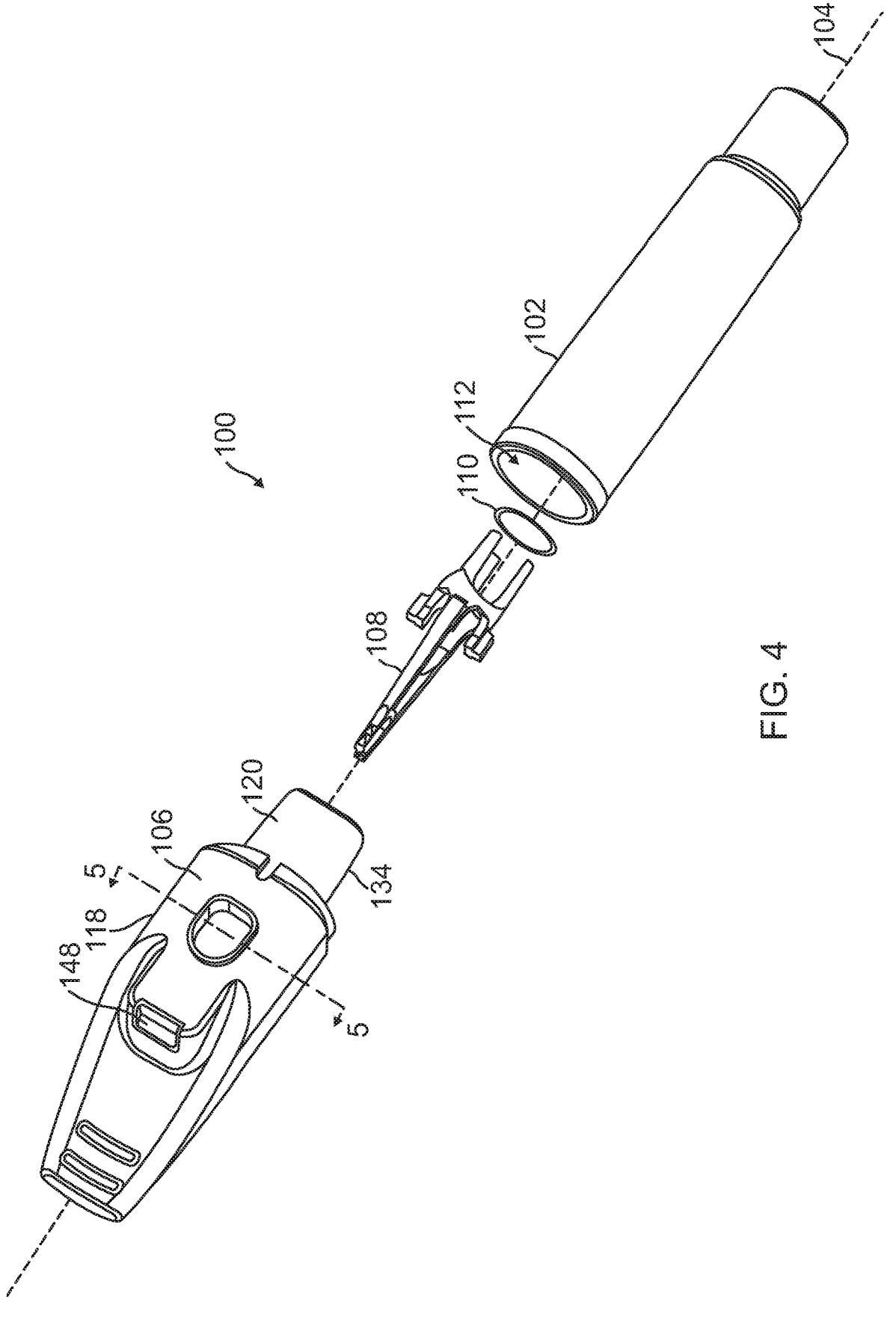
FIG. 4 depicts an exploded view of the biological indicator.

First portion 118 of cap 106 may comprise a third port 132 that provides access to recess 140. As such, as cap 106 is coupled to housing 102, third port 132 provides access to the inside of housing 102 via port 112 and a liquid passage that extends through a space disposed between sidewall 134, preferably flat portion 138 of sidewall 134, and inside surface 116 of housing 102. Arrow A is shown in FIG. 2 in this liquid passage to indicate the direction that liquid introduced through third port 132 would flow into housing 102.

First portion 118 of cap 106 may additionally include a detent 148, which may be useful for positioning biological indicator 100 in a decontamination system. That is, detent 148 may mate with a corresponding mating feature of the decontamination system such that third port 132 is positioned optimally for being mated with any tubing or flow connectors that may be used to deliver and withdraw liquids, e.g., decontaminants or neutralizers, into and out of housing 102. Because liquids introduced into housing 102 must be withdrawn therefrom to enable an accurate assessment of microbial outgrowth following the procedure, removal of liquids may be facilitated when biological indicator 100 is in a substantially horizontal position, i.e., substantially perpendicular to gravitational forces, with third port 132 facing down. A vent 150 may also be provided in cap 106, preferably in first portion 118. Vent 150 permits displacement of air from inside housing 102 by any liquids introduced thereto. Vent 150 also facilitates removal of liquids from inside housing 102, by allowing air to reenter housing 102 as the liquids are withdrawn.

Insert 108 is provided for two reasons. First, it helps maintain the position of carrier 110 at the bottom of housing 102. Second, it is used to pierce seal 128, which allows growth medium 124 to flow out of liquid chamber 122 and into housing 102 to immerse carrier 110. As best seen in FIG. 2, insert 108 includes a tip portion 152. Tip portion 152 may have the form of a spike, which may be forked, e.g., including two or more tines 154. Insert 108 may be fabricated of a suitable material, e.g., a polymer such as Cyclo-Olefin Polymer, and with tines 154 having a suitable form, e.g., a thickness of between about 0.2 mm and about 1 mm, e.g., about 0.5 mm, such that tines 154 may flex when subject to downward pressure. As such, when cap 106 is depressed downward, tip portion 152 pierces seal 128, which may be a film, such as a foil, e.g., aluminum foil. Upon initial contact between seal 128 and tip portion 152, tines 154 flex toward each other before the seal becomes punctured. Once seal 128 is punctured, tines 154 revert to their original position, thus enlarging the hole created in seal 128. Each tine 154 may additionally include surface features, e.g., ribs 156, which may further enlarge the hole in seal 128 as seal 128 moves downward over them.

By virtue of the embodiments illustrated and described herein, Applicant has devised a method and variations thereof for using a biological indicator of having those features described hereinabove. First, the biological indicator may be received by a user, e.g., by healthcare personnel. Then, the biological indicator may be disposed in a liquid-chemical decontamination system. In some variations, the biological indicator may be positioned in the chamber in a horizontal position. In further variations, it is positioned so the third port faces down. Next, the liquid decontaminant may be flowed into the housing via the third port in the cap. Subsequently, the liquid decontaminant may be removed from the housing via the third port in the cap. After the decontamination procedure is complete, the biological indicator may be removed from the chamber. Then, the cap may be depressed such that the seal becomes punctured by the top portion of the insert being driven through the seal, causing the growth medium in the liquid chamber of the cap to flow into the housing, through the puncture in the seal, to submerge the carrier. Simultaneously, vent 150 and third port 132 become blocked by housing 102.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A biological indicator, comprising:
   a housing; and
   a cap coupled to the housing, the cap including,
   a first portion disposed outside the housing,
   a second portion disposed at least partially inside the housing, the second portion including a sidewall, and
   a port disposed of the first portion, wherein the port provides access to a recess, disposed between the first portion and the second portion, wherein the recess has an irregular shape, formed at least in part by the sidewall and enlarged adjacent the port.

2. The biological indicator of claim 1, wherein the second portion includes the sidewall having a round portion and a flat portion, wherein the port and the recess are both located closer to the flat portion than the round portion.

3. The biological indicator of claim 2, wherein a liquid passage extends alongside the flat portion of the sidewall.

4. The biological indicator of claim 3, wherein the cap further comprises a detent.

5. The biological indicator of claim 4, in which the detent is disposed in the first portion of the cap.

6. The biological indicator of claim 1, wherein a liquid passage extends through a space disposed between the sidewall of the second portion of the cap and an inside surface of the housing.

7. The biological indicator of claim 1, in which the cap is coupled to the housing via a friction fit.

8. The biological indicator of claim 7, in which the friction fit comprises contact between an inner surface of the first portion of the cap and an outside surface of the housing.

9. The biological indicator of claim 1, wherein the second portion includes a liquid chamber containing a growth medium, and a seal defining a bottom boundary of the liquid chamber, wherein the seal comprises a film.

10. The biological indicator of claim 9, in which the film comprises a foil.

11. The biological indicator of claim 1, further comprising an insert disposed in the housing, the insert having a tip portion, wherein the tip portion comprises a spike.

12. The biological indicator of claim 11, in which the spike comprises a forked spike.

13. The biological indicator of claim 12, in which the forked spike includes at least two tines.

14. The biological indicator of claim 13, in which the at least two tines each includes at least one rib.

15. The biological indicator of claim 1, wherein the cap further includes a vent configured to permit displacement of air from inside the housing by any liquids introduced thereto via the port.

16. The biological indicator of claim 1, wherein the cap further includes a vent configured to facilitate removal of liquids from inside the housing, by allowing air to reenter the housing as any liquids are withdrawn via the port.

17. A method of using the biological indicator of claim 1, comprising:
   receiving the biological indicator;
   disposing the biological indicator in a chamber of a decontamination system;
   introducing, via a liquid passage inside the biological indicator, a liquid decontaminant into the housing through the port on the biological indicator; and
   removing, via the liquid passage inside the biological indicator, the liquid decontaminant from the housing through the port.

18. The method of claim 17, in which the step of disposing the biological indicator in the chamber comprises positioning the biological indicator in a substantially horizontal position.

19. The method of claim 18, in which the step of disposing the biological indicator in the chamber comprises positioning the biological indicator such that the port faces down.

20. The method of claim 19, further comprising:

removing the biological indicator from the chamber;

depressing the cap, coupled to the housing, relative to the housing; and puncturing a seal of the biological indicator covering a second port.

21. The method of claim 20, further comprising submersing a spore disk in a growth medium contained within the second port.

22. The method of claim 17, wherein the step of introducing further comprises:

displacing, via a vent on the biological indicator, air from inside the housing.

23. The method of claim 17, wherein the step of removing further comprises:

allowing air to enter the housing via a vent on the biological indicator.

\* \* \* \* \*